(12) United States Patent
Weinberger

(10) Patent No.: US 6,200,256 B1
(45) Date of Patent: Mar. 13, 2001

(54) APPARATUS AND METHOD TO TREAT A DISEASE PROCESS IN A LUMINAL STRUCTURE

(75) Inventor: Judah Z. Weinberger, Teaneck, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/271,063

(22) Filed: Mar. 17, 1999

(51) Int. Cl.⁷ ..................................................... A61N 5/00
(52) U.S. Cl. .................................. 600/3; 600/194
(58) Field of Search ...................... 600/1, 2, 3; 606/191, 606/192, 193, 194, 196, 197; 604/96, 97, 98, 99, 264

(56) References Cited

U.S. PATENT DOCUMENTS

| | | | |
|---|---|---|---|
| 5,059,166 | 10/1991 | Fischell et al. | 600/3 |
| 5,176,617 | 1/1993 | Fischell et al. | 600/3 |
| 5,213,561 | 5/1993 | Weinstein et al. | 600/7 |
| 5,302,168 | 4/1994 | Hess | 600/3 |
| 5,411,466 | 5/1995 | Hess | 600/3 |
| 5,683,345 | * 11/1997 | Waksman et al. | 600/3 |
| 5,720,717 | * 2/1998 | D'Andrea | 600/21 |
| 5,730,698 | * 3/1998 | Fischell et al. | 600/3 |
| 5,782,742 | 7/1998 | Crocker et al. | 600/3 |
| 5,840,008 | 12/1998 | Klein et al. | 600/3 |
| 5,865,720 | * 2/1999 | Hastings et al. | 600/3 |
| 5,879,282 | * 3/1999 | Fischell et al. | 600/3 |
| 5,947,889 | * 9/1999 | Hehrlein | 600/3 |
| 6,013,019 | * 1/2000 | Fischell et al. | 600/3 |
| 6,059,713 | * 5/2000 | Urick et al. | 600/3 |

* cited by examiner

Primary Examiner—Max Hindenburg
Assistant Examiner—Charles Marmor, II
(74) Attorney, Agent, or Firm—John P. White; Cooper & Dunham LLP (57) ABSTRACT

An apparatus and a method to treat a disease process in the vicinity of a luminal structure. Comprises a balloon catheter having a balloon and a tube segment of radioactive material located either inside the balloon or outside the balloon.

23 Claims, 4 Drawing Sheets

APPARATUS AND METHOD TO TREAT A DISEASE PROCESS IN A LUMINAL STRUCTURE

BACKGROUND OF THE INVENTION

The present invention relates to an apparatus and a method to treat a disease process in a luminal structure. Such a structure includes, but is not limited to, veins, arteries, bypass graft prostheses, the gastrointestinal (GI) tract, the biliary tract, the genitourinary (GU) tract, and the respiratory tract (e.g. the tracheobronchial tree).

Within this application several publications are referenced by Arabic numerals within parentheses. Full citations for these and other publications may be found at the end of the specification immediately preceding the claims. The disclosures of all of these publications in their entireties are hereby incorporated by reference into this application in order to more fully describe the state of the art to which this invention pertains.

Percutaneous transluminal coronary angioplasty ("PCTA") is commonly used in the treatment of coronary artery obstruction, with over 400,000 procedures performed annually. The process involves the insertion of balloon catheters through the femoral artery to the targeted coronary artery. Injection of radio-opaque contrast into the proximal coronary artery allows fluoroscopic localization of stenosed coronary segments. Balloon catheters are advanced to the site of stenosis over extremely thin guide wires to position the catheter at the point of occlusion. The distal end of the catheter contains a balloon which is inflated for 2–4 minutes to the full diameter of the occluded artery, decreasing the blockage and improving blood flow.

Approximately 40% of patients undergoing this procedure have angiographic evidence of restenosis by 12 months. The biological processes responsible for restenosis are not fully understood, but appear to result from abnormal proliferation of the "insulted" smooth muscle cells and neointima formation in the segment of treated artery (6). Although coronary artery blockage is a non-malignant disease, it has been suggested that treatment of the internal vessel walls with ionizing radiation could inhibit cell growth, and delay or even prevent restenosis (4, 7, 10–13).

Several groups have presented data demonstrating that 10–20 Gray of acute radiation delivered locally, via the temporary insertion of high activity gamma emitters at the time of angioplasty can inhibit restenosis in animal models (12,13). It has also been demonstrated that permanent radioactive coronary stents may be effective (10). Highly localized external beam therapy has been suggested as well (7,11). Most data to date have been obtained using animal models, but anecdotal reports suggest that radioactive treatment of human femoral arteries produces similar results (2). Preliminary human trials are being planned at several centers in the U.S. and Europe.

Preliminary studies have made use of currently available radioactive sources as none have been specifically designed for intracoronary treatments. Several manufacturers are considering modified High Dose Rate (HDR) afterloaders for this purpose.

Figure 1:
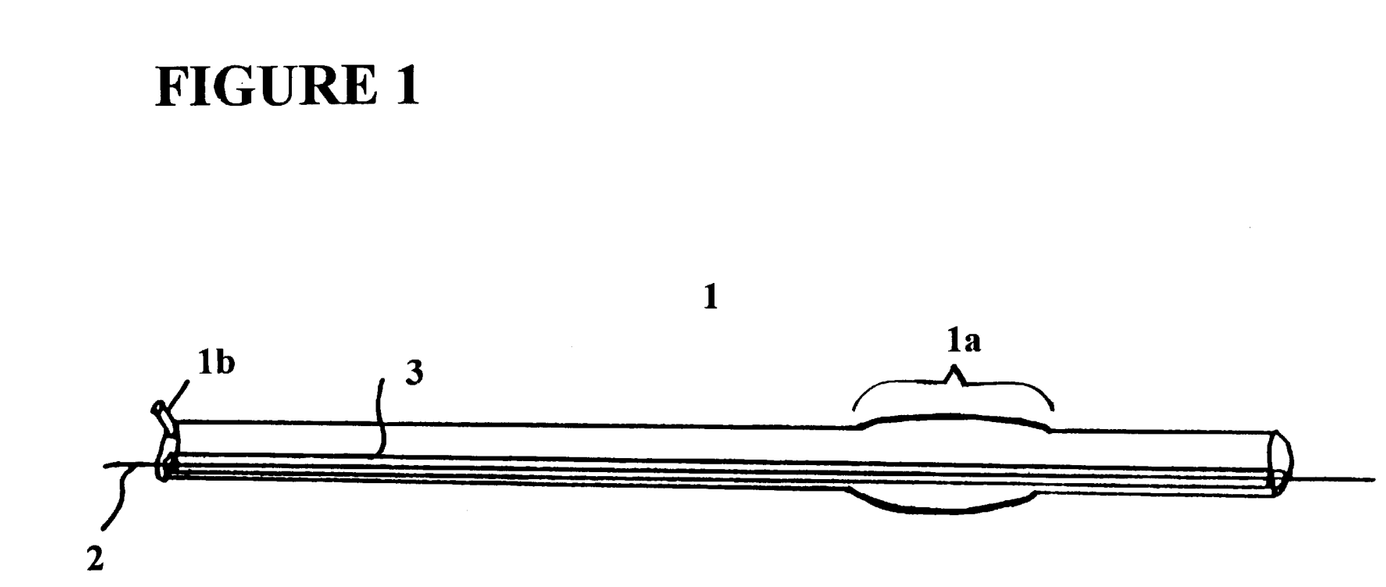
FIG. 1 shows the construction of a conventional over-the-wire type balloon catheter.

As stated above, restenosis after arterial intervention in general, PTCA in particular, seem to be primarily due to medial smooth muscle cell proliferation. Conventional PTCA is performed using a balloon catheter such an over-the-wire type catheter manufactured, for example, by Scimed Life Systems, Inc, of Maple Grove, Minn. or a mono-rail type catheter manufactured, for example, by Advanced Cardiovascular Systems, Inc, of Temecula, Calif. FIG. 1 depicts such a conventional over-the-wire balloon catheter 1. The conventional balloon catheter 1 is utilized in an angioplasty procedure as follows. A conventional guidewire 2 is inserted into the patient's artery until the distal end of the guidewire 2 is past a target area (not shown) of the artery (not shown) where there is a buildup of material. The conventional balloon catheter 1 has a lumen 3 running therethrough. The guidewire 2 is inserted into the distal end of the balloon catheter 1 and the balloon catheter 1 is advanced over the guidewire until the balloon section 1a of the balloon catheter 1 is adjacent the buildup of material. The balloon section 1a is then inflated by an inflation means (not show) connected to an inflation port 1b to clear the artery. Finally, the balloon section 1a is deflated, the balloon catheter 1 is pulled back up the guidewire and removed and the guidewire is likewise removed from the patient's artery.

Current technology contemplates different types of devices for the prevention of restenosis after arterial interventions. In one type, an arterial stent type is designed for long term deployment within the artery. Such a stent, if designed to emit radiation, would be in place long after the time necessary for the prevention of smooth muscle cell proliferation at the arterial site. U.S. Pat. No. 5,059,166 to Fischell describes such a long term stent.

Another type of device for preventing restenosis contemplates the delivery of unspecified doses of radiation via radioactive catheters and guidewires. These devices utilize a movable, flexible radiation shield. However, it is questionable whether such a radiation shield could be constructed given the thickness of material required to shield the radiation source and the flexibility required to allow delivery of the radiation source and shield to the coronary site. U.S. Pat. No. 5,213,561 to Weinstein relates to a device of this type.

Another type of device uses radioactive balloons which are typically inserted into a luminal structure in a deflated condition, and inflated with radioactive fluid after insertion. After a treatment period, the fluid is evacuated from the balloon and the device is removed. With such a system, there is always the risk that the balloon could rupture or leak resulting in radioactive fluid passing into the luminal structure.

SUMMARY OF THE INVENTION

It is an object of the present invention to provide an arrangement and method for treating a disease process or processes in a luminal structure or structures. Such structure or structures include, but are not limited to, veins, arteries, bypass graft prostheses, the gastrointestinal (GI) tract, the biliary tract, the genitourinary (GU) tract, and the respiratory tract (e.g. the tracheobronchial tree). The diseases to be treated by the invention include proliferative diseases (both malignant and non-malignant).

It is another object of the present invention to provide an arrangement for reducing restenosis after arterial or vascular intervention in a patient, or reducing proliferation from neoplastic or other proliferating diseases. Such intervention includes, but is not limited to, balloon angioplasty, atherectomy, stent placement, arterial grafts, and arteriovenous fistula.

It is a further object of the present invention to provide an arrangement for reducing restenosis after vascular intervention in the patient by delivering a dosage of radiation to the patient's artery at a target area.

It is a further object of the present invention to provide an arrangement for reducing restenosis after vascular intervention in the patient by delivering a radioactive dosage to the patient's artery at a target area while eliminating contact between the radioactive source and the patient's body fluids. One such way to eliminate contact is to position a radioactive source energy away from body fluids.

The present invention provides an alternative to a radioactive balloon delivery system for treating restenosis.

In accordance with the present invention, an apparatus and method are provided for treating a disease process inside a luminal structure. The present invention provides a tube segment to be used in conjunction with an angioplasty balloon catheter. The tube segment is adapted to be carried by and either cover or be covered by a balloon portion of a balloon catheter for insertion into the luminal structure. The tube segment includes radioactive material for producing radiation for treating a disease process.

According to one aspect of the present invention, a tube segment is provided for treating a disease process in a luminal structure. The tube segment includes radioactive material for delivering radiation for treating a disease process, and is adapted to be carried by a balloon catheter for insertion in the luminal structure.

According to another form of the invention, an apparatus for treating a disease process in a luminal structure is provided, comprising a balloon catheter having an inflatable balloon and a tube segment adapted to be carried by and cover said balloon. The tube segment includes radioactive material.

According to another form of the invention, an apparatus is provided for treating a disease process in a luminal structure, comprising a balloon catheter having a shaft with an inflatable balloon and a tube segment mounted on the shaft inside of said balloon, said tube segment including radioactive material.

According to another aspect of the invention, a method for treating a disease process in a luminal structure is provided comprising, inserting a balloon catheter into a luminal structure, said balloon catheter having an inflatable balloon and a tube segment containing radioactive material, inflating the balloon to contact the interior of the luminal structure, deflating the balloon and removing the balloon catheter after a desired radiation dose has been achieved.

According to another aspect of the invention, a method for treating a disease process in a luminal structure is provided comprising inserting a balloon catheter into a luminal structure, said balloon catheter having an inflatable balloon and an expansible tube segment on the outside of the balloon with radioactive material, inflating the balloon to thereby expand the tube segment, deflating the balloon causing the tube segment to reduce in size and removing the balloon catheter and tube segment from the luminal structure.

The radioactive material may be in the form of a coating on the tube segment. Alternatively or in addition, the tube segment may comprise a mixture of radioactive material and non-radioactive material. The tube segment may comprise non-radioactive material into which is absorbed radioactive material.

These and other advantages will become apparent from the detailed description, accompanying the claims and attached drawing figures.

DETAILED DESCRIPTION OF THE PREFERRED EMBODIMENTS

According to one aspect of the present invention, a tube segment is provided for treating a disease process in a luminal structure. The tube segment includes radioactive material for delivering radiation for treating a disease process, and is adapted to be carried by a balloon catheter for insertion in the luminal structure.

The radioactive material may be in the form of a coating.

The tube segment may comprise a mixture of radioactive material and non-radioactive material.

The tube segment may comprise non-radioactive material into which is adsorbed radioactive material.

The tube segment may be made of expandable and collapsible material, whereby its shape is determined by the shape of the balloon.

The tube segment may be located in the interior of or on the exterior of the balloon. If exterior, the tube segment has adhesive material on its inner surface, for adhesing the tube segment to a balloon.

If expandable, the radioactive material is present in a predetermined dosage per surface area of the tube segment when the tube segment is in an unexpanded state, wherein the dosage changes as the tube segment is inflated.

The sleeve may be expandable in a range of sizes.

According to another form of the invention, an apparatus for treating a disease process in a luminal structure is provided, comprising a balloon catheter having an inflatable balloon and a tube segment adapted to be carried by and cover said balloon. The tube segment includes radioactive material.

The tube segment may be attached to the balloon or shaft by heat sealing or adhesive or may constitute the terminal portion of a long tubular catheter which can be independently moved along the balloon catheter.

According to another form of the invention, an apparatus is provided for treating a disease process in a luminal structure, comprising a balloon catheter having a shaft with an inflatable balloon and a tube segment mounted on the shaft inside of said balloon, said tube segment including radioactive material.

According to another aspect of the invention, a method for treating a disease process in a luminal structure is provided comprising, inserting a balloon catheter into a luminal structure, said balloon catheter having an inflatable balloon and a tube segment containing radioactive material, inflating the balloon to move the tube segment closer to the interior of the luminal structure, deflating the balloon and removing the balloon catheter after a desired radiation dose has been achieved.

According to another aspect of the invention, a method for treating a disease process in a luminal structure is provided comprising inserting a balloon catheter into a luminal structure, said balloon catheter having an inflatable balloon and an expansible tube segment on the outside of the balloon with radioactive material, inflating the balloon to thereby expand the tube segment, deflating the balloon causing the tube segment to reduce in size and removing the balloon catheter and tube segment from the luminal structure.

The tube segment used with the balloon may be selected from a plurality of differently sized tube segments, activities, and isotope sources.

According to another aspect of the invention, a balloon catheter has a balloon mounted on its distal end, the balloon being expandable and contractable upon filling and evacuating the balloon using fluid, which fluid can be a gaseous phase, liquid phase, or combination. The catheter may have one or more lumens for receiving a guide wire for locating and positioning the balloon catheter in or near luminal structure of a patient, for treating a disease process in the lumen such as plaque. The catheter may not have any guidewire lumen.

The invention may be used to treat or prevent a disease process. As used herein, the term "treat" or "treating" is used in its broad sense and includes inhibiting and preventing a disease process or condition, as well as treating in the narrow sense.

The invention may be used to treat a luminal structure or areas in the vicinity of a luminal structure. As used herein the term "vicinity of a luminal structure" includes areas adjacent to or in proximity with, as well as the luminal structure itself.

The balloon alone is neither made of nor does it contain any radioactive material. However, a tube segment is provided which is radioactive. The tube segment may be located inside the balloon or outside the balloon. The tube segment has radioactive material as an ingredient or coating, or has had radioactive material absorbed into the tube segment. If coated, the tube segment may be coated on the inner cylindrical surface or outer cylindrical surface. If absorbed, the tube segment could be treated by exposing it to a radioactive isotope species. For a tube segment inside the balloon, the segment composition could include a radioactive metallic sheet or metallic coil attached to the catheter shaft.

While it is preferred that the radioactive material be applied to the tube segment at the time of manufacture, it may be applied at the time of use by the user, at least for the embodiment wherein the tube segment is located outside the balloon. A host of methods for attaching radioactive moieties to plastic surfaces are known. In general, proteins, nucleic acids, and smaller molecules may be adsorbed either covalently or by ionic bonding to various plastics (15–17). Also existing are techniques to radioactively modify proteins or nucleic acids (18–24). For additional plastic composition and radioactive source bonding data see (25) and the documents cited therein. The material of the sleeve may require physical modification, such as flame treatment, corona or plasma treatments, ultraviolet laser, x-ray, gammaray, electron beam, ion beam treatments, metallization or sputtering. In order to immobolize the radioactive source (or sources) the material of the sleeve may also require chemical modification such as Web treatments, including, but not limited to, etching of fluoropolymers, surface oxidation and etching, hydrolysis, and functionalization, or surface grafting. Depending upon ultimate isotope species utilized polymer blend surface or block copolymer surfaces may be advantageous.

Examples of radioisotopes that may be used are radio isotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay, and may be selected from the group consisting of NA-24, SI-31, K-42, SC-43, SC-44, CO-55, MN-56, CU-61, NI-65, GA-66, GA-68, ZN-71, GA-72, AS-72, SE-73, BR-75, AS-76, BR-76, GE-77, KR-77, AS-78, Y-85, KR-87, ZR-87, NB-89, Y-90, NB-90, SR-91, Y-92, Y-93, ZR-97, IN-110, AG-112, AG-113, SB-122, SN-127, TE-129, BA-139, LA-140, LA-141, LA-142, PR-142, PR-145, TB-148, PM-150, EU-152, HO-166, RE-188, RE-190, IR-194, BI-212, and radioactive sodium-chloride.

In a typical use, doses of 5—5 Gray should be applied to a length of 2–60 cm of the vessel wall, which is 1–8 mm in diameter. The dose distribution should preferably be tightly confined to the region of the angioplasty, with greatly reduced doses to normal vessels and the myocardia or nearby organs. Typical dose rates on the order of 0.5–50 Gray/minute should preferably be used in order to limit treatment times within tolerable limits particularly in to coronary tree.

Figure 2:
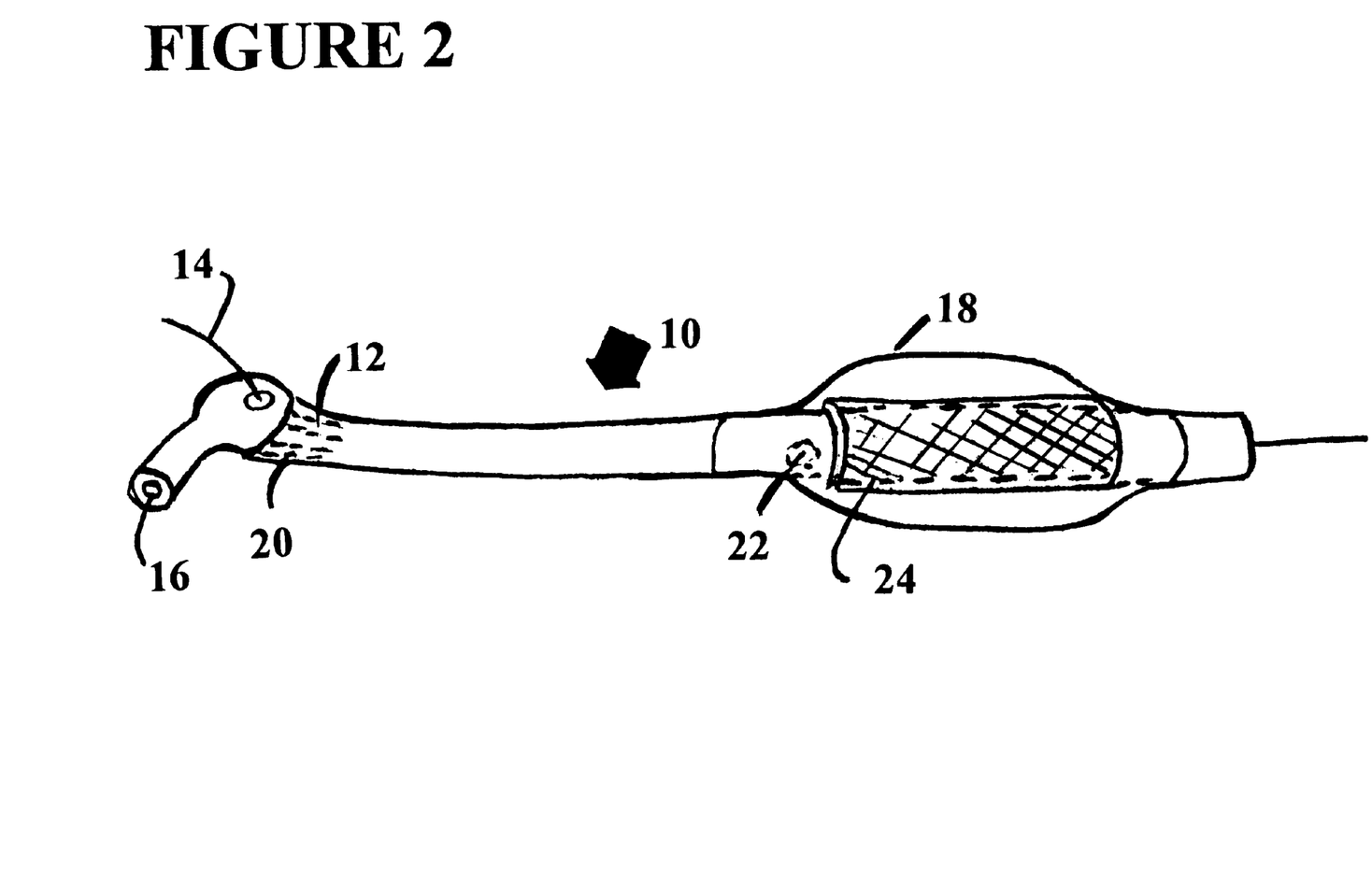
FIG. 2 shows the construction of a radioactive tube segment with balloon catheter according to a first embodiment of the present invention.

FIG. 2 shows a balloon catheter according to a first embodiment of the present invention, which can also be used to perform the method according to the present invention. The apparatus is particularly suited for delivering radioactive doses to the coronary artery. The preferred embodiment will be described with reference to the coronary artery, but this is by way of example, and not limitation, as the present invention may also be used to deliver radiation to or from other luminal structures.

The apparatus comprises a balloon catheter 10 with a guidewire lumen 12 extending entirely through the balloon catheter 10. The guidewire lumen 12 is sized to fit around a guidewire 14 and to allow the guidewire 14 to slide therein. The length of guidewire 14 is sufficient to allow it to extend past a target segment of the artery and it may be, for example, greater than about 110 cm for use in the coronary artery. For use in other arteries, the length of guidewire 14 may also be greater than about 110 cm or it may be less.

The outside diameter of the guidewire 14 may be about 0.014 inch and in this case the inside diameter of the guidewire lumen 12 is slightly larger, to permit movement of the balloon catheter 10 over the guidewire 14. Of course, as mentioned above, the catheter need not have a guidewire lumen.

A balloon inflation port 16 allows inflation of the balloon section 18 at the distal end of the balloon catheter 10 in the conventional manner.

Inflation port 16 is in communication, through a lumen 20 in the catheter, to port 22 located in the inside of the balloon 18.

Disposed inside the balloon 18 is a tube segment 24. The tube segment 24 contains radioactive material, either integral, absorbed, adsorbed, coated or in any other manner to integrate or combine it with the tube segment 24.

Figure 3:
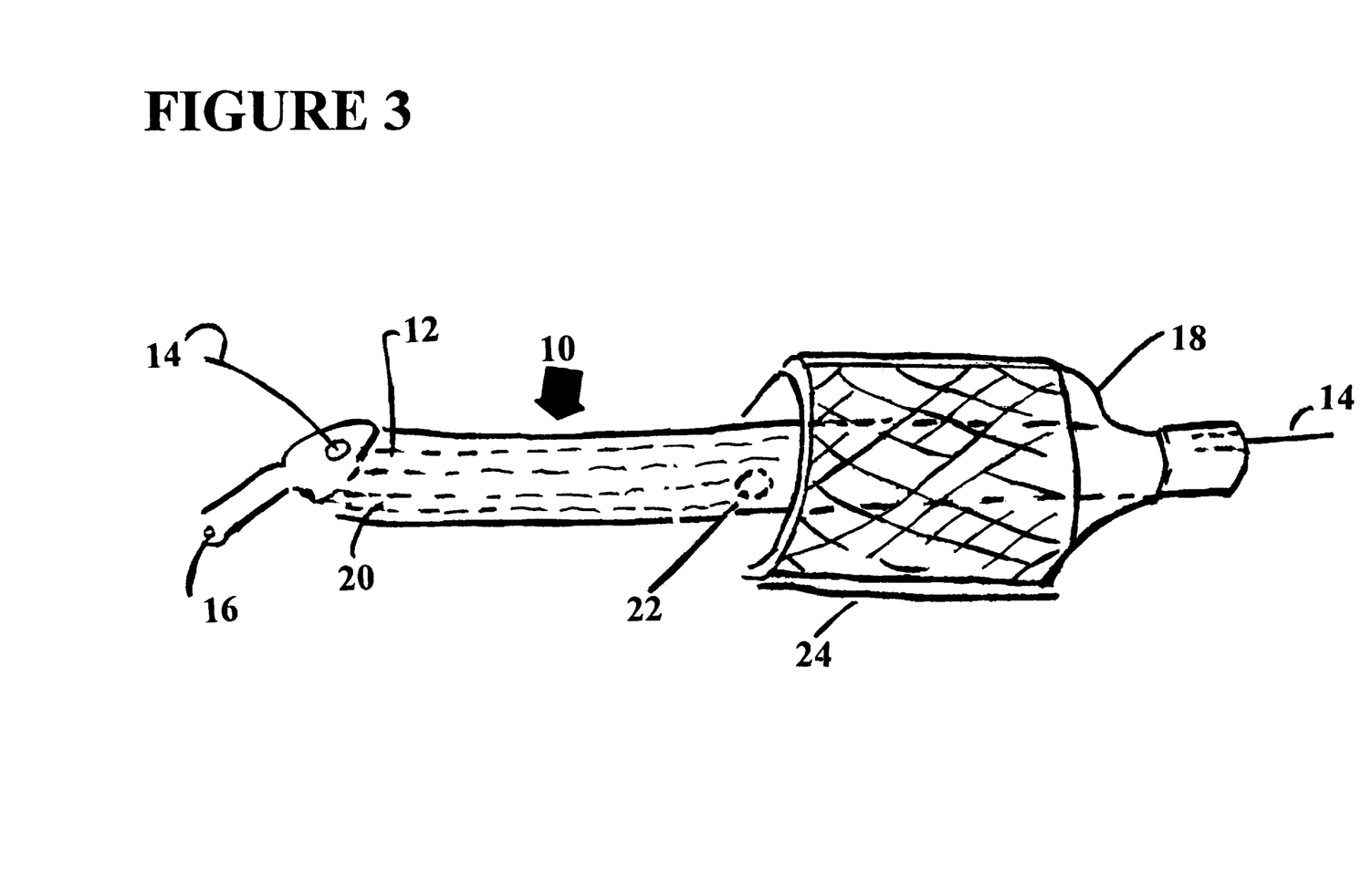
FIG. 3 shows the construction of a radioactive tube segment with balloon catheter according to a second embodiment of the present invention.

FIG. 3 shows another embodiment of a balloon catheter with a tube segment, except in contrast to the embodiment of FIG. 2, here the tube segment is located on the outside of the balloon.

If the tube segment is outside to the balloon, the tube segment may be expansible and collapsible, having its shape and size determined by the balloon. The tube segment may be attachable to the balloon by adhesive material or by heat sealing.

The tube segment may be formed by employing a polymer material incorporating a fairly long half life radioisotope (preferably a beta emitter) which is extruded in a tube form, which is then cut to form a tube segment. The tube segment is annealed to a balloon angioplasty shaft and subsequently a balloon covering may be placed over the shaft.

Figure 4:
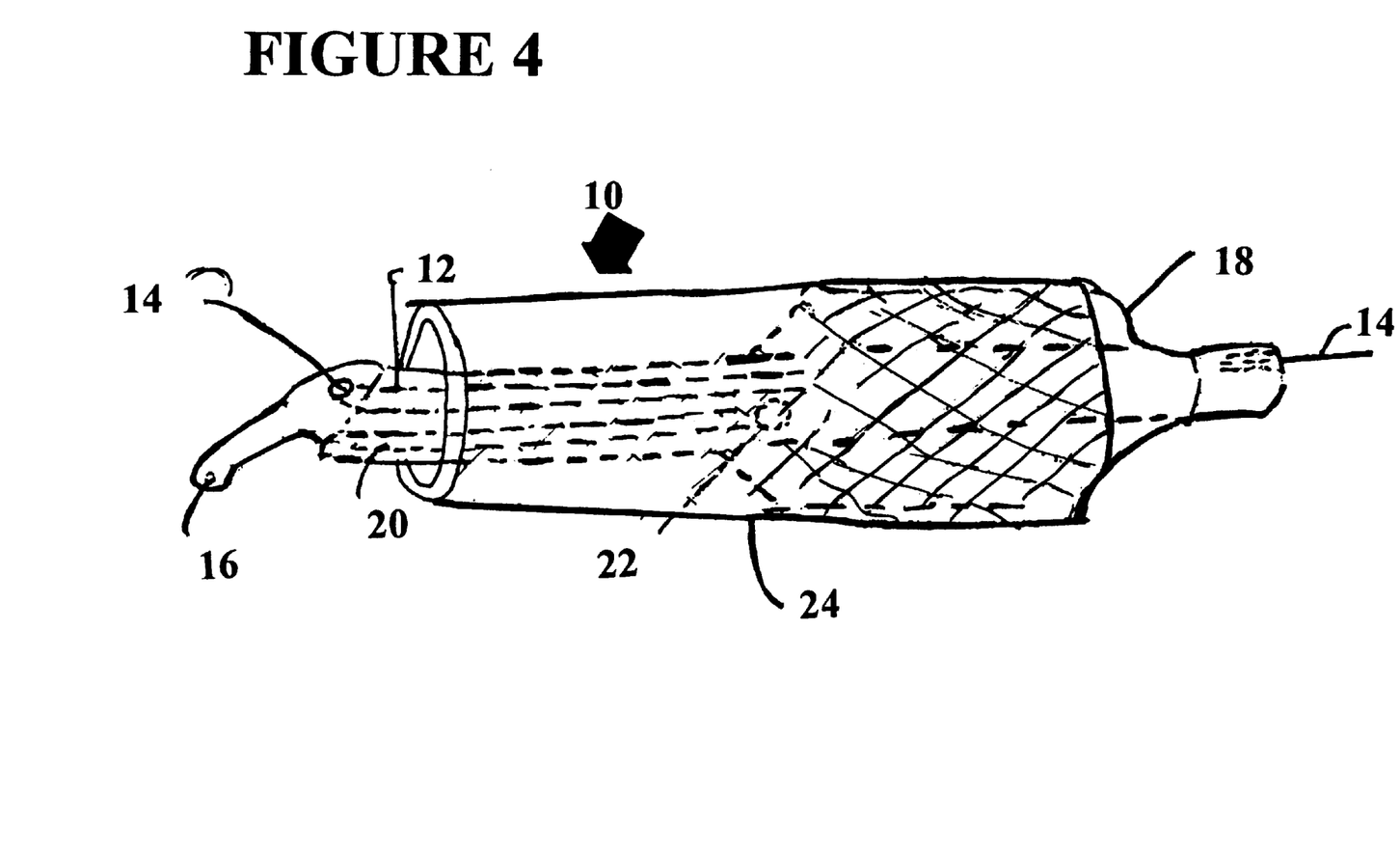
FIG. 4 shows the construction of a tube segment as part of a tube according to a third embodiment of the invention.

Alternatively, the tube segment may be moveable and radioactive only in its distal portion. The balloon would be positioned first, followed by positioning of an exterior tube, the distal end of which is radioactive and comprises the tube segment, as shown in FIG. 4, wherein the tube segment having radioactive material is shown hatched, the remainder of the tube unhatched and not having radioactive material.

The radioactivity may be on the order of 5–500 millicuries per centimeter length. Optionally the balloon would be highly compliant, allowing one standard balloon size to accommodate arterial diameters of 1.5 to 8 mm. Alternatively, it may be desireable to use non-compliant material and have different sized tube segments for each sized balloon. The inner tube segment member containing the radioisotope would not be inflated, and is located away from the inflation lumen for the balloon. Thus, the balloon, rather than the tube segment, is directly inflatable. To improve treatment times, the balloon catheter may be inflated using inert gas such as $CO_2$ or Argon. This would reduce the amount of intracatheter absorption of beta particles prior to entering the vessel wall.

The tube segment or conduit preferably has the shape such that its inner and outer walls are concentric, with equal or substantially equal wall thickness around its circumference and longitudinal lengths. However, it may be desirable in some cases to have an eccentric tube with unequal wall thickness around its circumference or to have the wall thickness otherwise vary around its circumference and/or along its length. In this way the radiation dose may vary axially or longitudinally.

For a tube segment which is positioned outside the balloon, the tube segment or conduit is extruded, possibly using a relatively high complaint material having a minimum radioresistance value of $2.5 \times 10^6 Gy$. A central length portion of the tube of a length of about 1–60 cm has its surface activated with a radio-isotope. One example of such an activation process is using a plasma or a chemical coating. The isotope solution is brought into contact with the activated surface to allow adsorption, absorption or bonding with tube segment. The tube segment is then rinsed and dried. The tube segment or portion thereof may then be mounted over an existing balloon on the shaft of angioplasty catheter. The ends of the tube segment may be attached to the balloon or catheter shaft by adhesive bonding or heat sealing. The tube segment may thus be inflated indirectly by inflating the balloon inside the tube segment.

For a tube segment or coil which is mounted inside of a balloon, the tube segment should preferably be positioned at the target site of an angioplasty catheter prior to the balloon being mounted to the catheter. To start, the tube segment is extruded from a material such as plastic containing a radioactive isotope or coated as described above, or a metallic tube segment is activated or impregnated with radioisotope. The dimensions of the tube segment are substantially the same as the dimensions of the catheter shaft in the radial direction, and comparable to the active balloon length (e.g., 5 mm–60 cm) in the longitudinal direction. The tube segment material may be a polymer containing a radioisotope of, e.g. $p^{32}$ or $Y^{90}$, and is thus itself radioactive.

The tube segment is then positioned on the shaft of a catheter and is annealed to the shaft, clear of the inflation port. A balloon may then be positioned over the segment of the shaft carrying the radioactive tube segment and attached to the shaft such as by annealing. The balloon is mounted over the inflation port, so that the balloon may be inflated by an inflation gas such as Ar or $Co_2$. The balloon material may be a highly elastic radiation resistant polymer.

For both types of tube segments, i.e., exterior and interior to the balloon, because the radioactive isotope is affixed to the solid phase of the tube segment, risk of patient contamination with radioisotope is minimized, even if the balloon ruptures, compared to radioactive inflation fluid approach.

For both types of tube segments, there is no need for additional hardware, such as an afterloader with its typical attendant costs of $250–350 k, to position solid, high activity radioactive sources in the blood vessel.

The invention provides minimal radiation disposal problems for users. A user may simply cut off the distal portion of the catheter containing the radioactive material and place the cut off portion in a radioactive waste disposal container for decay. The remaining body of the catheter is non-radioactive and may be handled routinely.

An interior mounted tube segment according to the invention has advantages compared to a liquid balloon because a tube segment poses essentially no risk of radioactive contamination of a patient in the event of balloon rupture. The tube segment may be prepared in a controlled factory environment, compared to a balloon which is dose filled on site by the end user and thus subject to variance in dose rates.

As used herein, the term "distensibility" refers to the ability to vary ultimate balloon diameter over a range of sizes, e.g. diameter of 1.5–5 mm, based on pressure of inflating medium, i.e. liquid and/or gas.

The present invention provides potential distensibility, dosing, and safety advantages. Considering the same distensible balloon with fixed radioactive coating in a 2 mm diameter artery versus a 4 mm diameter artery, the density of radioactive material varies approximately proportional to $1/r^2$, where r is the radius. Thus the dose rate will be at least four fold slower. Therefore, radiation dosing in a small vessel will be significantly briefer in duration than in a large vessel.

The invention provides various ways to incorporate a radioactive isotope in or on a tube segment. One such way is by charge coating radioisotope material to the tube segment. For anionic radioisotopes, the surface of an extruded tube segment may be treated to produce a strongly cationic surface, for example, with polyethylenimine (PEI) with or without plasma treatments. Descriptions of such treatments may be found in U.S. Pat. No. 4,332,916 which is incorporated by reference herein. The anionic radioisotope solution is subsequently applied. Colloidal silica in small amounts may be added to increase the capacity for anions.

To coat a tube segment for use external to the balloon the following process may be employed. The tube segment is first extruded as a tube. The inner surface of the tube can then optionally be plasma treated, following the teachings of, e.g., U.S. Pat. No. 5,296,714, which is incorporated herein by reference. The surface of the tube is then coated with material to produce a cationic (or anionic) surface, e.g. PEI. The tube is then dried. The tube is then incubated with anionic (or cationic) radioisotope solution, and then rinsed and dried. The resultant tube or tube segment may then be mounted over the existing balloon.

An internal tube segment for use inside a balloon may be made according to the following process. A tube or tube segment is first extruded having a diameter comparable to the shaft of the balloon catheter, with the extruded material including radioisotope as a complex. The typical activity of the radioactive isotope may be 1 millicurie to 1 curie per cm length. The typical length of the tube segment may be 5 mm to 50 cm. The tube segment is then mounted onto the shaft and is sealed. The balloon is then mounted over the shaft and tube segment. An inflation/deflation port is provided to inflate/deflate the balloon.

The operation of an apparatus to reduce restenosis after arterial intervention according to the first embodiment of the present invention may be as follows. First a guidewire is inserted into the patient's artery. The distal end of the guidewire is inserted at least as far as, and preferably past the target site, that is, the site that is to receive the dose of radiation. The near end of the guidewire is then inserted into the guidewire lumen and the balloon catheter is moved down the guidewire towards the distal end until the balloon section and tube segment are adjacent the target site. The balloon section may then inflated and deflated by balloon inflation/deflation inflation means connected to the balloon inflation port.

The radioactive tube segment may be left in place until a desired dosage of radiation has been delivered to the target area. The length of time that the tube segment is left adjacent the target area depends upon the activity of its radioactive sources the diameter of the artery at the target area, and the desired dosage to be delivered.

Alternatively, a guidewire may be inserted into the artery as described above and a conventional balloon catheter (without a tube segment) is placed over the guidewire and advanced to the target area to be inflated, deflated, and removed from the artery. After removal from the artery, the balloon catheter of the instant invention, now with the tube segment, may be placed over the guidewire utilizing the guidewire lumen and located adjacent the target area in order to allow the tube segment to deliver a dosage of radiation to the target area as described above. This procedure permits the use of a conventional balloon catheter to perform an angioplasty procedure before the tube segment of the instant invention is utilized to deliver a dose of radiation.

The inventive device and method may also be applied to delivery of radiation in and around other luminal structures in a similar manner.

The present invention provides for delivery of radioactive material in non-fluid form, which minimizes the risk of patient exposure to radioactive fluid due to rupture removes the operator from the vicinity of the radioactive fluid, and reduces the reduces the risk of a spill of radioactive fluid.

The balloon portion of the catheter may be formed of a medical plastic material typically chosen from the group consisting of polyethylene, PET, and Nylon.

It must be noted that although the present invention is described by reference to particular embodiments thereof, many changes and modifications of the invention may become apparent to those skilled in the art without departing from the spirit and scope of the invention as set forth in the claims.

References

1. Berger, M. J. and Seltzer, S. M. Stopping powers and ranges of electrons and positrons (2nd Ed.). U.S. Dept. Commerce Publication NBSIR 82-2550-A (1983)

2. Bottcher, H. D., Schopohl, B., Liermann, D., Kollath, J., and Adamietz, I. A. Endovascular irradiation-a new method to avoid recurrent stenosis after stent implantation in peripheral arteries: technique and preliminary results. *Int. J. Rad. Onc. Biol. Phys.* 29, 183–186 (1994)

3. Friedell, H. L., Thomas, C. I., and Krohmer, J. S. Description of an $Sr^{90}$ beta-ray applicator and its use on the eye. *Amer. J. Roentg.* 65, 232–245 (1951)

4. Gellman, J., Healey G., Qingsheng, C., Tselentakis, M. J. The effects of very low dose irradiation on restenosis following balloon angioplasty. A study in the atherosclerotic rabbit. *Circulation* 84, Supple 11, 46A–59A (1991)

5. Johns, H. E., and Cunningham, J. R.. The Physics of Radiology (4th Edition). Charles Thomas, Publisher (Springfield, Ill., 1983).

6. Landau, C., Lange, R. A., Hillis, L. D. Percutaneous transluminal coronary angioplasty. *NEJM* 330, 981–993 (1994)

7. Mayberg, M. R., Luo, Z., London, S., Gajdusek, C., Rasey, J. S. Radiation inhibition of intimal hyperplasia after arterial injury. *Rad. Res.* 142, 212–220 (1995)

8. MIRD. Method of calculation: "S", absorbed dose per unit cumulated activity for selected radionuclides and organs. *MIRD Pamphlet* #11 (1975).

9. Nath, R., Anderson, L., Luxton, G., et. al. Dosimetry of interstitial brachytherapy sources: recommendations of the AAPM radiation therapy committee task group No. 43. *Med. Phys.* 22, 209–234 (1995)

10. Prestwich, W. V., Kennet, T. J., and Kus, F. W. The dose distribution produced by a $P^{32}$-coated stent. *Med. Phys.* 22, 313–320 (1995)

11. Schwartz, R. S., Koval, T. M., Edwards, W. D., Camrud, A. R., Bailey, K. R., Brown, K., Vlietstra, R. E., and Holmes, D. R. Effect of external beam irradiation on neointimal hyperplasia after experimental coronary artery injury. *J. Am. Col. Cardiol.* 19, 1106–1113 (1992).

12. Wiederman, J., Marobe, C., Amols, H., Schwartz, A., and Weinberger, J. Intracoronary irradiation markedly reduces restenosis after balloon angioplasty in a porcine model. *J. Amer. Col. Card.* 23, 1491–8 (1994)

13. Wiederman, J., Leavy, J., Amols, H., Schwartz, A., Homma, S., Marobe, C., and Weinberger, J. Effects of high dose intracoronary irradiation on vasomotor function and smooth muscle histopathology. *Am. J. Phys. (Heart and Circ. Physiol.)* 267, H125–H132 (1994)

14. Williamson, J. F., and Zuofend, L. Monte carlo aided dosimetry of the microselectron pulsed and high dose-rate $^{192}$Ir sources. *Med. Phys.* 22, 809–819 (1995)

15. Desai, N. P., & Hubbell, J. A. (1991). Biological responses to polyethylene oxide modified polyethylene terephthalate surfaces. *Journal of Biomedical Materials Research*, 25(7), 829–43.

16. Gombotz, W. R., Wang, G. H., Horbett, T. A., & Hoffman, A. S. (1991). Protein adsorption to poly (ethylene oxide) surfaces. *Journal of Biomedical Materials Research*, 25(12), 1547–62.

17. Massia, S. P., & Hubbell, J. A. (1991). Human endothelial cell interactions with surface-coupled adhesion peptides on a nonadhesive glass substrate and two polymeric biomaterials. *Journal of Biomedical Materials Research*, 25(2), 223–42.

18. Afshan, A., Jehangir, M., Ashraf, M., Waqar, A., & Chiotellis, E. (1994). Formulation of a single-component kit for the preparation of technetium-99m labeled ethyl cysteinate dimer; biological and clinical evaluation. *European Journal of Nuclear Medicine*, 21(9), 991–5.

19. Hannant, D., Bowen, J. G., Price, M. R., & Baldwin, R. W. (1980). Radioiodination of rat hepatoma-specific antigens and retention of serological reactivity. *British Journal of Cancer*, 41(5), 716–23.

20. Hartikka, M., Vihko, P., Sodervall, M., Hakalahti, L., Torniainen, P., & Vihko, R. (1989). Radio labeling of monoclonal antibodies: optimization of conjugation of DTPA to F(ab')2-fragments and a novel measurement of the degree of conjugation using Eu(III)-labeling. *European Journal of Nuclear Medicine,* 15(3), 157–61.

21. Ingvar, M., Eriksson, L., Rogers, G. A., Stone, E. S., & Widen, L. (1991). Rapid feasibility studies of tracers for positron emission tomography: high-resolution PET in small animals with kinetic analysis. *Journal of Cerebral Blood Flow & Metabolism,* 11(6), 926–31.

22. Portoles, P., Rojo, J. M., & Janeway, C. J. (1990). A simple method for the radioactive iodination of CD4 molecules. *Journal of Immunological Methods,* 129(1), 105–9.

23. Samuel, D., Amlot, P. L., & Abuknesha, R. A. (1985). A new method of iodinating ovalbumin, a protein which lacks accessible tyrosine groups, by conjugation to a highly fluorescent coumarin active ester, CASE. *Journal of Immunological Methods,* 81(1), 123–30.

24. Wafelman, A. R., Konings, M. C., Hoefnagel, C. A., Maes, R. A., & Beijnen, J. H. (1994). Synthesis, radiolabelling and stability of radioiodinated m-iodobenzylguanidine, a review. [Review]. *Applied Radiation & Isotopes,* 45(10), 997–107

25. Polymers FAQ, Polymers archive on the Internet complied by Jim Coffey, Aug. 11, 1995.

26. Abayomi, O., Chun, M., & Ball, H. (1990). Stage II carcinoma of the cervix: analysis of the value of pretreatment extraperitoneal lymph node sampling and adjunctive surgery following irradiation. *Radiotherapy & Oncology.* 19(1), 43–7.

27. Ampil, F. L. (1985). Primary malignant neoplasm of the female urethra. *Obstetrics & Gynecology.* 66(6), 799–804.

28. Beauvois, S., Hoffstetter, S., Peiffert, D., Luporsi, E., Carolus, J. M., Dartois, D., & Pernot, M. (1994). Brachytherapy for lower lip epidermoid cancer: tumoral and treatment factors influencing recurrences and complications. *Radiotherapy & Oncology,* 33(3), 195–203.

29. Broga, D. W., & Gilbert, M. A. (1983). A review of three incidents involving the release of 125I from seeds interstitially implanted within the prostate gland. *Health Physics.* 45(3), 593–7.

30. Cotter, G. W., Lariscy, C., Ellingwood, K. E., & Herber, D. (1993). Inoperable endobronchial obstructing lung cancer treated with combined endobronchial and external beam irradiation: a dosimetric analysis. *International Journal of Radiation Oncology. Biology. Physics.* 27(3), 581–5.

31. George, F. (1980). Radiation management in esophageal cancer. With a review of intraesophageal radioactive iridium treatment in 24 patients. *American Journal of Surgery,* 139(6), 795–804.

32. Lavery, I. C., Jones, I. T., Weakley, F. L., Saxton, J. P., Fazio, V. W., & Jagelman, D. G. (1987). Definitive management of rectal cancer by contact (endocavitary) irradiation. *Diseases of the Colon & Rectum,* 30(11), 835–8.

33. Leung, J. T., & Kuan, R. (1995). Brachytherapy in oesophageal carcinoma. *Australasian Radiology,* 39(4), 375–8.

34. Rosenshein, N. B. (1983). Radioisotopes in the treatment of ovarian cancer. *Clinics in Obstertrics & Gynecology,* 10(2), 279–95.

35. Volterrani, F., Prosperini, G., Sigurta, D., Vona, S., Musumeci, R., Milani, A., & Luciani, L. (1979). Present status of treatment for invasive cervical carcinoma. *Tumori,* 65(5), 611–24.

36. Spencer, R. P., Nuclear medicine and therapy: a reorientation to specificity and beta ray generators, Symposium on Therapy in Nuclear Medicine, 3–15, (1978).

37. Knapp, F. F., Callahan, A. P., Beets, A. L., Mirxadeh, S., and Hsieh, B. T., Processing of reactor-produced $^{188}$W for fabrication of clinical scale alumina-based $^{188}$W/$^{188}$Re generators, Appl. Radiat. Isot., 45:1123–1128 (1994).

38. Johns, H. E., and Cunningham, J. R.. The Physics of Radiology (4th Edition). Charles Thomas, Publisher (Springfield, Ill., 1983).

39. Berger, M. J. and Seltzer, S. M., Stopping powers and ranges of electrons and positrons, 2nd ed., U.S. Dept. Of Commerce Publications NBSIR 82-2550-A, (1983).

40. Friedell, H. L., Thomas, C. I., and Krohmer, J. S. Description of an $Sr^{90}$ beta-ray applicator and its use on the eye. *Amer. J. Roentg.* 65, 232–245 (1951).

41. Simpkin, D. J. and Mackie, T. R., EGS Monte Carlo determination of the beta dose kernel in water, Med. Phys., 17:179–186 (1990).

42. McLaughlin, W. L, Chen. Y. D, Soares, C. G., Miller, A., VanDyck, G., and Lewis, D. F., Sensitometry of the response of a new radiochromic film dosimeter to gamma radiation and electron beams, Nucl. Instrum. Meth. Phys. Res., A 302:165–176 (1991).

43. Berger, M. J., Distribution of absorbed dose around point sources of electrons and beta particles in water and other media, MIRD Pamphlet No. 7, J. Nucl. Med. 12, Suppl. NO. 5, 5–24 (1971).

I claim:

1. An apparatus for treating a disease process in the vicinity of a luminal structure, comprising:
 a balloon catheter having a shaft and an inflatable balloon; and
 a tube having a distal tube segment adapted to cover said balloon, said tube segment including radioactive material, said tube being radioactive only at its distal tube segment.

2. The apparatus according to claim 1, wherein the tube segment comprises radioactive material in the form of a coating.

3. The apparatus according to claim 1, wherein the tube segment comprises a mixture of radioactive material and non-radioactive material.

4. The apparatus according to claim 1, wherein the tube segment comprises non-radioactive material into which is absorbed radioactive material.

5. The apparatus according to claim 1, wherein the tube segment is adhesively attached to the balloon or catheter shaft.

6. The apparatus according to claim 1, wherein the tube segment is attached to the balloon or catheter shaft by heat sealing.

7. An apparatus for treating a disease process in the vicinity a luminal structure, comprising:
 a balloon catheter having a shaft and an inflatable balloon; and
 a tube having a tube segment mounted on the balloon, said tube segment including radioactive material, said tube being radioactive only at its tube segment.

8. The apparatus according to claim 7, wherein the tube segment comprises radioactive material in the form of a coating.

9. The apparatus according to claim 7, wherein the tube segment comprises a mixture of radioactive material and non-radioactive material.

10. The apparatus according to claim 7, wherein the tube segment comprises non-radioactive material into which is absorbed radioactive material.

11. The tube segment according to claim 7, wherein the tube segment is made of expandable and collapsible material, whereby its shape may be determined by the shape of the balloon.

12. The tube segment according to claim 11, wherein the radioactive material is present in a predetermined dosage per surface area of the tube segment when the tube segment is in an unexpanded state, but wherein the dosage changes as the tube segment is inflated.

13. The tube segment according to claim 7, wherein the tube segment has adhesive material on its inner surface, for adhesing the tube segment to the balloon or catheter shaft.

14. The tube segment according to claim 7, wherein the tube segment is expandable in a range of sizes.

15. The apparatus of claim 7, wherein the tube segment is sheathed in foil.

16. The apparatus of claim 7, wherein the tube segment comprises a coil.

17. The apparatus of claim 7, wherein the tube segment is impregnated with a radioisotope.

18. The apparatus of claim 7, wherein the tube segment is coated with a radioisotope.

19. A method for treating a disease process in the vicinity of a luminal structure comprising:

inserting a balloon catheter into a luminal structure, said balloon catheter having an inflatable balloon;

inserting a tube having a tube segment which includes radioactive material, but which is not otherwise radioactive, so that the tube segment is located over the balloon;

inflating the balloon with fluid to move the tube segment closer to the interior of the luminal structure to administer a radiation dose to the luminal structure;

deflating the balloon and tube segment; and removing the tube after a desired radiation dose has been achieved.

20. The method, according to claim 19, wherein the step of inflating comprises inflating the balloon with gaseous media.

21. The method according to claim 20, wherein the gaseous media is selected from the group comprising $Co_2$ and Argon.

22. A method for treating a disease process in the vicinity of a luminal structure comprising:

inserting a balloon catheter into a luminal structure, said balloon catheter having an inflatable balloon;

inserting a tube having an expansible tube segment on the outside of the balloon, said tube having radioactive material only at the tube segment;

inflating the balloon to thereby expand the tube segment and administer a radiation dose to the luminal structure;

deflating the balloon causing the tube segment to reduce in size; and removing the tube from the luminal structure.

23. The method of claim 22, further including the step of providing a plurality of tubes having tube segments with differently sized tube segments and dosages;

selecting a tube having the tube segment of a desired size and dose; and mounting the selected tube with the desired tube segment on the catheter.

* * * * *